United States Patent [19]

Baiel et al.

[11] Patent Number: 5,718,808
[45] Date of Patent: Feb. 17, 1998

[54] SOLVENT ASSISTED PROCESS FOR RECOVERY OF PHTHALIC ANHYDRIDE IN THE LIQUID PHASE BY DISTILLATION

[75] Inventors: James J. Baiel, Morris Plains, N.J.;
Larry O. Jones, Baton Rouge, La.;
Ralph D. Gray, Jr., Morristown, N.J.;
Magdiel Agosto, Baton Rouge, La.

[73] Assignee: Exxon Chemical Patents Inc., Houston, Tex.

[21] Appl. No.: 758,558

[22] Filed: Nov. 29, 1996

[51] Int. Cl.⁶ .................................................. C07D 307/89
[52] U.S. Cl. ............................ 203/56; 203/51; 549/250
[58] Field of Search ....................... 203/51, 56; 549/248, 549/249, 250

[56] References Cited

U.S. PATENT DOCUMENTS

| | | | |
|---|---|---|---|
| 3,178,452 | 4/1965 | Smith et al. | 260/346.4 |
| 3,303,203 | 2/1967 | Melnstein | 260/346.7 |
| 3,380,896 | 4/1968 | Scheiber et al. | 203/77 |
| 3,397,121 | 8/1968 | Fitzgerald | 203/35 |
| 3,507,886 | 4/1970 | Suter et al. | 260/346.7 |
| 3,650,906 | 3/1972 | Gehrken et al. | 203/89 |
| 3,655,521 | 4/1972 | Gehrken et al. | 203/28 |
| 3,681,399 | 8/1972 | Barth | 260/346.7 |
| 3,725,211 | 4/1973 | Gehrken et al. | 203/74 |
| 4,285,870 | 8/1981 | Keunecke et al. | 260/346.7 |
| 4,285,871 | 8/1981 | Keunecke et al. | 260/346.7 |
| 4,568,427 | 2/1986 | Danz et al. | 203/42 |
| 5,214,157 | 5/1993 | Healy et al. | 549/250 |

FOREIGN PATENT DOCUMENTS

| | | | |
|---|---|---|---|
| 1121645 | 4/1956 | France | 14/1 |

*Primary Examiner*—Timothy McMahon
*Attorney, Agent, or Firm*—John F. Hunt; Richard D. Jordan

[57] ABSTRACT

A process for recovering phthalic anhydride as a liquid from a vapor phase oxidation product which comprises mixing the vapor phase oxidation product having a temperature of about 130° C. or greater with a first stream comprising a solvent having a boiling point in the range between about 150° to 350° C. and a freezing point of less than 40° C., and, optionally, at least one by-product selected from the group consisting of: maleic anhydride, citraconic anhydride, benzoic acid and phthalic anhydride, in a contacting means such that a substantial portion of the phthalic anhydride contained within the vapor phase oxidation product transfers from the vapor phase to a liquid phase and a substantial portion of the first stream which are more volatile than phthalic anhydride transfer from the liquid phase to the vapor phase and wherein a vapor-to-liquid weight ratio in the range between about 2 to 20 is exhibited within the contacting means, thereby forming a liquid phase phthalic anhydride product having a phthalic anhydride concentration in the range between about 50–100 wt. %., preferably 90–100 wt. %, without the formation of an intermediate solid phase.

24 Claims, 5 Drawing Sheets

SOLVENT ASSISTED PROCESS FOR RECOVERY OF PHTHALIC ANHYDRIDE IN THE LIQUID PHASE BY DISTILLATION

The present invention generally relates to a method and system for continuously recovering liquid phase phthalic anhydride from a vapor phase oxidation product without the formation of a solid phase. In particular, phthalic anhydride is recovered from the vapor phase oxidation product by contacting this gaseous oxidation product with a solvent and, optionally, recycled maleic anhydride and other by-products, in a rectification tower so that the condensate does not solidify and so that a vapor-to-liquid weight ratio in the range between about 2 to 20 is maintained, thereby eliminating the need for switch condensers. In this way the more volatile by-products are taken overhead from the separation vessel as a vapor, while phthalic anhydride is taken out as bottoms without the formation of a solid phase during the separation. The unique solvent is one which lowers the freezing point of the rectification tower liquid distillate and enlarges the operating region.

BACKGROUND OF THE INVENTION

Phthalic anhydride is an important commercial chemical useful in the manufacture of plasticizers, polyesters, alkyd resins and dyes.

Phthalic anhydride is typically produced from raw materials such as orthoxylene (o-xylene), petroleum naphthalene, and coal-tar naphthalene. Various well known processes are currently being used in the production of phthalic anhydride, i.e., (1) air oxidation of o-xylene in fixed-bed reactors, (2) air oxidation of petroleum or coal tar naphthalene in fixed-bed reactors, (3) fluid bed oxidation of o-xylene, (4) fluid bed oxidation of petroleum or coal tar naphthalene, and (5) liquid phase oxidation of o-xylene or naphthalene.

U.S. Pat. No. 5,214,157 (Healy et at.), which issued on May 25, 1993, is incorporated herein by reference and generally discloses the formation of phthalic anhydride via the vapor phase oxidation of o-xylene. In accordance with the process described in U.S. Pat. No. 5,214,157, o-xylene and air are catalytically converted into a vapor phase oxidation product, i.e., a reaction gas composed of nitrogen, oxygen, water, carbon dioxide, carbon monoxide, phthalic anhydride, maleic anhydride, maleic acid, benzoic acid, o-toluic acid, and partial oxidation products such as phthalide. This vapor phase oxidation product is typically first cooled to generate steam and then delivered to expensive switch condensers, where it is cooled to permit the desublimation of a crude phthalic anhydride stream from the gas. Thereafter, the crude phthalic anhydride is sent to a finishing section in order to produce substantially pure phthalic anhydride.

The switch condensers operate alternatively on cooling and heating cycles in order to first collect the phthalic anhydride as a solid and then melt it for removal from the condensers. The use of switch condensers to separate crude phthalic anhydride from a vapor phase oxidation product is also described in U.S. Pat. No. 5,214,157, which is incorporated herein by reference. Typically, the reactor vapor phase oxidation product is cooled close to the solidification point 131° C. (268° F.) of phthalic anhydride and any condensed liquid is separated out before the remaining vapor enters the switch condensers. The switch condensers desublime the vapor phase oxidation product using the cold condenser oil, and then melt off the solid phase crude phthalic anhydride product using a hot condenser oil heated with steam.

A substantial amount of impurities exit switch condensers as part of the vapor stream, whereas the crude phthalic anhydride product is plated out on the heat exchange tubes as a solid during the cooling step and exits the switch condensers at the bottom as a liquid during the melting step. The vapor gases from the switch condensers are sent to waste gas incinerators where the by-products are destroyed by oxidation to carbon dioxide and water.

Unfortunately, switch condensers contribute to a significant portion of the capital and operating costs of a phthalic anhydride plant. Also, switch condensers operate in a batch mode on 3–6 hours cycles to desublime solid phthalic anhydride on the heat exchange tubes. Another problem associated with switch condensers is that they necessitate frequent maintenance which requires that designated switch condensers be taken out of service on a periodic basis. Maintenance of switch condensers is costly due to the high labor requirement and condenser down time.

The present inventors have developed a unique process scheme which avoids the need to use expensive switch condensers to recover the phthalic anhydride from the vapor phase oxidation product. This unique process continuously condenses and recovers phthalic anhydride by rectification without the formation of an intermediate solid phase, wherein the more volatile by-products are taken overhead. This liquid phthalic anhydride recovery process using a rectification tower is disclosed in co-pending U.S. Patent Application, Ser. No. 08/43 1,647 (Dengler et al.), filed on May 2, 1995, and which is incorporated herein by reference. Another liquid phthalic anhydride recovery process is disclosed in U.S. Patent Application, Ser. No. 08/241,876 (Dengler), filed May 12, 1994, which is also incorporated herein by reference.

The liquid phthalic anhydride recovery process disclosed in U.S. Patent Application, Ser. No. 08/431,647, (Dengler et al.) is based on concentating the indigenous maleic anhydride (MAN), citraconic anhydride (CAN) and benzoic acid (BA) co-products produced in the phthalic anhydride (PAN) reactor to form a low freezing point liquid MAN/BA/PAN/CAN mixture in the rectification tower condenser system. The present inventors have discovered that the condensing temperature is critical to the liquid phthalic anhydride recovery process and must: (1) be low enough to recover sufficient MAN and CAN; (2) high enough to insure the liquid distillate will not freeze; and (3) be high enough to avoid free water from condensing thereby forming excessive amounts of acids in the distillate.

The optimum condensing temperature depends on other process variables, but generally falls between 37.8 and 48.9° C. (100° and 120° F.) for the reasons stated above. The estimated ternary MAN/BA/PAN eutectic temperature is reasonably low at approximately 39.4° C. (103° F.); however, the operating region around this eutectic (i.e., 40.5° C. (105° F.) isotherm) is undesirably small. Operating at higher temperatures in the overhead (i.e., 43.3° C. (110° F.)) enlarges the operating region, but requires a MAN recovery unit to maintain the high MAN concentrations required.

The liquid phthalic anhydride recovery process disclosed in the above co-pending application is generally directed to: (1) a method of recovering phthalic anhydride without the use of switch condensers in a cyclic process of cooling and heating; (2) a method where the vapor phase reaction product from the vapor phase oxidation of o-xylene or naphthalene to phthalic anhydride and by-products is contacted in a rectification tower with a liquid condensate from a condenser, the liquid condensate containing phthalic anhydride and reaction by-products; (3) where the freezing point of the liquid condensate is lower than the freezing point of phthalic anhydride; and (4) operating with the gas temperature in the distillation tower and condenser always above the melting point of the mixture.

A requirement for these conventional liquid phthalic anhydride recovery processes is that the selectivity to by-products from the reaction of o-xylene or naphthalene to phthalic anhydride and by-products is such that sufficient by-products are produced to form a phthalic anhydride and by-products condensate that has desired freezing point characteristics for the process. The main by-products of the current commercially available catalysts are products such as maleic anhydride, benzoic acid, citraconic anhydride, phthalide and o-tolualdehyde.

Another requirement of the conventional liquid phthalic anhydride recovery process is that the by-products be produced in sufficient quantity that at the target liquid phase distillate composition the amount produced is in balance with the amount that leaves the gas stream exiting the condenser. If not, an additional recovery step is required to recover and recycle the by-products.

Further, the balance of by-products depends on the concentration of o-xylene or naphthalene in the feed gas (i.e., air plus o-xylene or naphthalene). For example, processes with higher concentrations of o-xylene or naphthalene will produce more phthalic anhydride and by-products per unit of air feed. With higher concentrations of by-products per unit of air, there will be a smaller percentage of these products leaving the condenser at any given gas temperature leaving the condenser.

Thus, it is easier for processes having higher o-xylene or naphthalene concentrations in the feed gas to the oxidation reactor to maintain the required concentration and amount of these materials in the liquid recovery process without additional recovery steps.

The concentration of maleic anhydride and citraconic anhydride in the liquid phthalic anhydride recovery process is a direct function of selectivity of the phthalic anhydride catalyst. However, since the thrust in future phthalic anhydride process developments is toward higher phthalic anhydride selectivities and less maleic anhydride and citraconic anhydride, the amount of maleic anhydride and citraconic anhydride available for the liquid phthalic anhydride recovery process may be destined to become less and less, thereby limiting the operating range of the rectification tower. Thus, for some current catalysts (and for future catalysts) there may not be sufficient maleic anhydride and citraconic anhydride produced to maintain the appropriate freezing point condensate.

Catalysts are known to produce different types and yields of reaction products. The type of reaction products will also vary with the feed to the oxidation reaction. For example, naphthalene feed produces naphthoquinone as one by-product not found with o-xylene feed.

Therefore, the present inventors have developed a modification to the liquid phthalic anhydride recovery process disclosed in co-pending U.S. Patent Application, Ser. No. 08/431,647, (Dengler et al.). The present invention provides for the addition of a solvent to the rectification tower reflux system to lower the freezing point of the liquid PAN/MAN/BA/CAN mixture. In addition, the solvent according to the present invention will increase the low temperature operating region and broaden the potential application of the liquid phthalic anhydride recovery process. In essence, the solvent can be used to replace or eliminate by-product materials that are not produced in the reactor in sufficient quantity because of the relatively low concentration of o-xylene in the feed, the low selectivity of the catalyst to by-products or the amount of by-products leaving the condenser in the gas stream. Moreover, the addition of solvent according to the present invention does not significantly change the gas/liquid ratio in the rectification tower.

In summary, using a specifically tailored solvent in the liquid phthalic anhydride recovery process: (1) allows for the choosing of a tailored component which reduces the freezing point of the liquid maleic anhydride/benzoic acid/phthalic anhydride/citraconic anhydride eutectic mixture; (2) provides a low freezing point operating region sufficiently large for good commercial plant operation and control; (3) frees the liquid phthalic anhydride recovery process from depending solely on the maleic anhydride, citraconic anhydride and benzoic acid in the phthalic anhydride gas feed to reduce the freezing point; and (4) eliminates the need for a maleic anhydride/citraconic anhydride recovery unit on the incinerator gas.

SUMMARY OF THE INVENTION

A process for recovering phthalic anhydride as a liquid from a vapor phase oxidation product which comprises mixing the vapor phase oxidation product having a temperature of about 130° C. or greater with a first stream comprising a solvent having a boiling point in the range between about 150° to 350° C. and a freezing point of less than 40° C., and, optionally, at least one by-product selected from the group consisting of: maleic anhydride, citraconic anhydride, benzoic acid and phthalic anhydride, in a contacting means such that a substantial portion of the phthalic anhydride contained within the vapor phase oxidation product transfers from the vapor phase to a liquid phase and a substantial portion of the first stream which are more volatile than phthalic anhydride transfer from the liquid phase to the vapor phase and wherein a vapor-to-liquid weight ratio in the range between about 2 to 20 is exhibited within the contacting means, thereby forming a liquid phase phthalic anhydride product having a phthalic anhydride concentration in the range between about 50–100 wt. %, preferably 90–100 wt. %, without the formation of an intermediate solid phase.

More preferably, the solvent has a boiling point in the range between about 200° to 285° C., more preferably 213° to 270° C. The solvent is at least one solvent selected from the group consisting of: adipates, maleates, phthalates, carbonates, benzoates, ketones, aromatics, anhydrides, esters halogenated hydrocarbons, halogenated oxy hydrocarbons, ether acetates, naphthalenes and ethers.

A preferred embodiment using low solvent addition together with by-product reflux according to the present invention involves a process for recovering phthalic anhydride as a liquid from a vapor phase oxidation product which comprises: (a) cooling the vapor phase oxidation product to a temperature of about 130° C. or greater; (b) delivering the vapor phase oxidation product to a contacting means which is capable of causing the vapor phase oxidation product to come into contact with a solvent having a boiling point in the range between about 150° to 350° C. and a freezing point of less than 40° C. and at least one by-product stream having a freezing point which is lower than the freezing point of pure phthalic anhydride such that a substantial portion of the phthalic anhydride contained within the vapor phase oxidation product transfers from the vapor phase to a liquid phase and a substantial portion of the by-product stream is more volatile than phthalic anhydride transferred from the liquid phase to the vapor phase and wherein a vapor-to-liquid weight ratio in the range between about 2 to 20 is exhibited within the contacting means, thereby forming a liquid phase phthalic anhydride product having a phthalic anhydride concentration in the range between about 50 to 100 wt. %, and a first vapor stream; the contacting means is also capable of separating the liquid phase phthalic anhydride product from the first vapor stream; (c) removing the liquid phase phthalic anhydride product from the contacting means as bottoms; (d) removing the first vapor stream from the contacting means as overhead; (e) cooling the first vapor stream to a temperature in the range between about 25° C. to 80° C., thereby forming the solvent, a first by-product stream and a second vapor stream; (f) separating the solvent and the first by-product stream from the second vapor stream; and (g) recycling at least a portion of the solvent and the first by-product stream to the upper section of the contacting means. Preferably, the maleic anhydride to phthalic anhydride ratio in the vapor phase oxidation product is sufficient to cause freezing in the first by-product stream, i.e., the maleic anhydride to phthalic anhydride ratio in the first by-product stream is less than or equal to 0.07 to 1.

The solvent is preferably present in an amount between about 1 to 50 mole based upon the total amount of the solvent and first by-product stream recycled under step (g). The process further comprises the step wherein make-up solvent is also added.

A preferred embodiment using all or high solvent addition reflux according to the present invention involves a process for recovering phthalic anhydride as a liquid from a vapor phase oxidation product which comprises: (a) cooling the vapor phase oxidation product to a temperature of about 130° C. or greater; (b) delivering the vapor phase oxidation product to a contacting means which is capable of causing the vapor phase oxidation product to come into contact with a solvent having a boiling point in the range between about 150° to 350° C. and a freezing point of less than 40° C. such that a substantial portion of the phthalic anhydride contained within the vapor phase oxidation product transfers from the vapor phase to a liquid phase and a substantial portion of the solvent is transferred from the liquid phase to the vapor phase and wherein a vapor-to-liquid weight ratio in the range between about 2 to 20 is exhibited within the contacting means, thereby forming a liquid phase phthalic anhydride product having a phthalic anhydride concentration in the range between about 50 to 100 wt. %, and a first vapor stream; the contacting means is also capable of separating the liquid phase phthalic anhydride product from the first vapor stream; (c) removing the liquid phase phthalic anhydride product from the contacting means as bottoms; (d) removing the first vapor stream from the contacting means as overhead; (e) cooling the first vapor stream to a temperature in the range between about 25° C. to 80° C., thereby forming the solvent, a first by-product stream and a second vapor stream; (f) separating the solvent and the first by-product stream from the second vapor stream; (g) separating the solvent from the first by-product stream thereby forming a third vapor stream and a solvent-enriched stream; (h) recycling at least a portion of the solvent-enriched stream to the upper section of the contacting means; (i) diverting at least a portion of the solvent-enriched stream; (j) separating the diverted solvent-enriched stream into a fourth vapor phase comprising at least solvent and a second by-products stream comprising at least benzoic acid; (k) recycling the fourth vapor phase to the upper section of the contacting means; and (l) combining the second by-product stream with the liquid phase phthalic anhydride product. Preferably, the maleic anhydride to phthalic anhydride ratio in the vapor phase oxidation product is sufficient to cause freezing in the first by-product stream, i.e., the maleic anhydride to phthalic anhydride ratio in the first by-product stream is less than or equal to 0.07 to 1.

DESCRIPTION OF THE PREFERRED EMBODIMENTS

A continuous process for recovering phthalic anhydride (PAN) in a liquid phase from a vapor phase oxidation product of o-xylene, naphthalene or the like, and compressed air is hereafter described.

The freezing point of pure phthalic anhydride is 131° C. (268° F.). Conventional switch condensers operate by cooling the vapor phase oxidation product below this temperature to plate out solid phase phthalic anhydride on the heat exchange tubes within each switch condenser.

According to a first embodiment of the present invention, the formation of crude liquid phthalic anhydride product without the presence of an intermediate solid phase phthalic anhydride is accomplished by contacting the vapor phase oxidation product with a solvent having a boiling point in the range between about 150° to 350° C. and a freezing point of less than 40° C. and recycled by-products which have lower freezing points than pure phthalic anhydride, whereby the operating temperatures are always above the freezing point of the liquid phase. It is preferable that the contacting occur in a rectification tower so that a vapor-to-liquid weight ratio within the contacting tower is maintained in the range between about 2 to 20, more preferably 8 to 15.

Thus, it is a primary objective of the present invention to add a specifically tailored solvent to the liquid phthalic anhydride processes described below which is capable of lowering the freezing point of the phthalic anhydride/maleic anhydride/benzoic acid eutectic mixture. In addition, the present inventors have discovered that the uniquely tailored solvent will increase the low temperature operating region and broaden the potential application of the liquid phthalic anhydride process.

SOLVENTS

A good solvent candidate must exhibit the following properties: (1) have good solvency for the mixtures so as to achieve maximum freezing point depression at low solvent concentrations; (2) have a volatility lower than citraconic anhydride so as to minimize the solvent lost to the incinerator gas, but higher than benzoic acid to enable recovery and recycle of any solvent that breaks through the liquid phthalic anhydride tower as bottoms; (3) have a low pure component freezing point; and (4) be chemically inert under process conditions.

The most desirable solvents for the liquid phthalic anhydride recovery process are those with an aromatic ring and/or oxygen in the structure. These types of solvent structures promote solubility of the phthalic anhydride, maleic anhydride, citraconic anhydride and benzoic acid in the solvent. The solvents are those which have a boiling point in the range between about 150° to 350° C., more preferably 200° to 285° C., and most preferably 213° to 270° C., and a freezing point of less than 40° C.

The present inventors have discovered that the best solvents have a melting point lower than the cooling medium used to condense liquid and produce a liquid reflux to the rectification tower, have good solvency for phthalic anhydride and reaction by-products, and have a vapor pressure that allows separation by distillation of solvent from phthalic anhydride and reaction by-products.

The best solvent family groups are adipates, maleates, phthalates, carbonates, benzoates, ketones, aromatics, anhydrides, esters, halogenated hydrocarbons, halogenated oxy hydrocarbons, ether acetates, naphthalenes and ethers.

Set forth below are preferred solvents in each of the above-identified solvent families along with their boiling and freezing points:

| Solvent | Boiling Point (°C.) | Freezing Point (°C.) |
|---|---|---|
| ADIPATES | | |
| dimethyl adipate | 235 | 0 |
| CARBONATES | | |
| propylene carbonate | 242 | −49 |
| BENZOATES | | |
| propyl benzoate | 229 | −52 |
| isobutyl benzoate | 242 | |
| KETONES | | |
| isophorone | 215 | −8 |
| e-caprolactone | 235 | −2 |
| isobutyl heptyl ketone | 213–224 | −10 |
| di-normal amyl ketone | 228 | 14 |
| di-isoamyl ketone | 226 | 15 |
| AROMATICS | | |
| hexyl benzene | 226 | −61 |
| narrow cut mixed aromatics solvent (Aromatic 200 range) | | −26 |
| ANHYDRIDES | | |
| n-valeric anhydride | 227 | −49 |

| Solvent | Boiling Point (°C.) | Freezing Point (°C.) |
|---|---|---|
| ESTERS | | |
| $C_9$ alky acetate ester | 205–234 | −60 |
| $C_{10}$ alky acetate ester | 220–250 | −60 |
| 1,4-butanediol diacetate | 229 | 12 |
| malonic acid-dipropyl ester | 229 | −70 |
| phthalic acid-dimethyl ester | 282 | 2 |
| maleic acid-dimethyl ester | 205 | −19 |
| maleic acid-diethyl ester | 225 | −88 |

Additionally, esters formed from the reaction product of $C_5$ to $C_{10}$ neo acids and $C_2$ to $C_{10}$ monohydric or polyhydric alcohols may also be used to lower the freezing point of the liquid condensate which is taken overhead from the contacting means, thereby avoiding freezing thereof.

According to the present invention solvent addition allows a wider range in concentration for the reaction products. In addition, solvent can be added in less than 50 percent or greater than 50 percent to the reaction products in the liquid condensate.

For some purposes, it is advantageous to add the minimum mount of solvent as required by the process (less than 50% added solvent). The amount of solvent required is controlled by the temperature of the reflux, the reflux ratio, the selectivity by-products and the solvent properties. This minimum is set by having sufficient solvent present to achieve a freezing point sufficiently low that the cooling medium in the condensing means can both condense the liquid and cool the gas in an economically sized exchanger. In addition, the by-products entering and leaving the liquid recovery process must be in balance. Using less than 50% added solvent minimizes the mount of added solvent that leaves the liquid recovery process and that must be added as make-up or recovered from one of the exit streams.

In other cases, it may be advantageous to have mostly solvent (i.e., greater than 50%) in the reflux to the rectification tower. The exact balance of solvent to reaction products will depend on the process conditions, including catalyst selectivity, that exactly balance the amount of by-products produced in the reactor with the amount leaving the gas from the condenser. In these high solvent cases, the concentration of phthalic anhydride and reaction by-products will be proportionately decreased.

One particular advantage for the high solvent or all solvent case relates to reactions that can occur between reaction products in the rectification tower and condenser (i.e., PAN, MAN, BA, CAN, ortho-tolualdehyde and water). Maleic anhydride and citraconic anhydride tend to be more reactive materials than phthalic anhydride. For example, they can react with the water produced in the oxidation reaction and form acids. Maleic acid can then isomerize to fumaric acid. Fumaric acid is a known color former in the production of phthalic anhydride. Citraconic anhydride can undergo similar reactions. Thus, it is advantageous to keep the concentrations of these materials low in the liquid recovery process streams. This is accomplished by having a high percentage of solvent in the reflux to the rectification tower.

Figure 1:
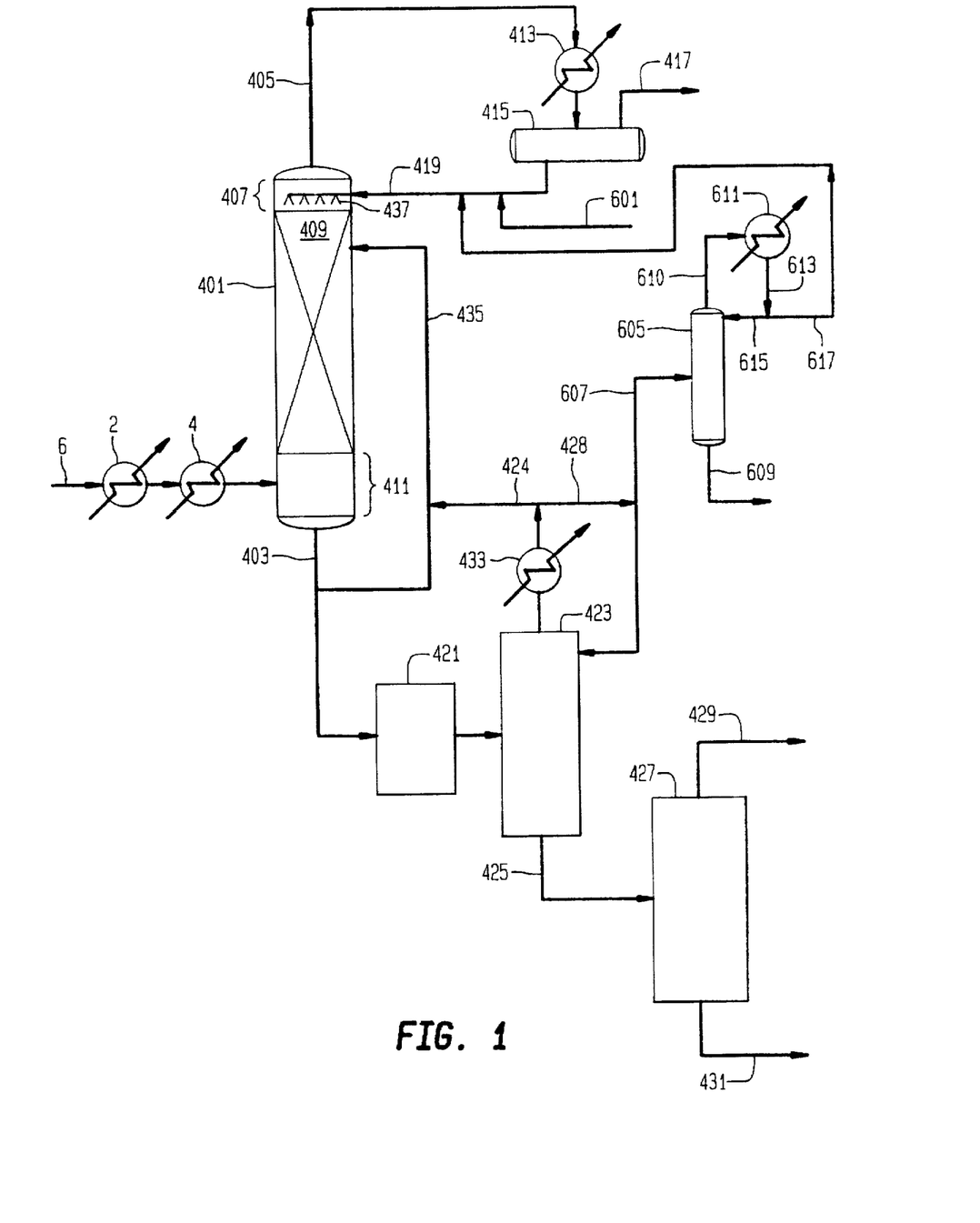
FIG. 1 is a schematic diagram of the phthalic anhydride recovery process in accordance with a preferred embodiment of the present invention wherein a low pressure gas/liquid contactor rectification tower is used in conjunction with external cooling and separating devices for recycling refluxed low freezing point solvent and by-products to the rectification tower.
Figure 2:
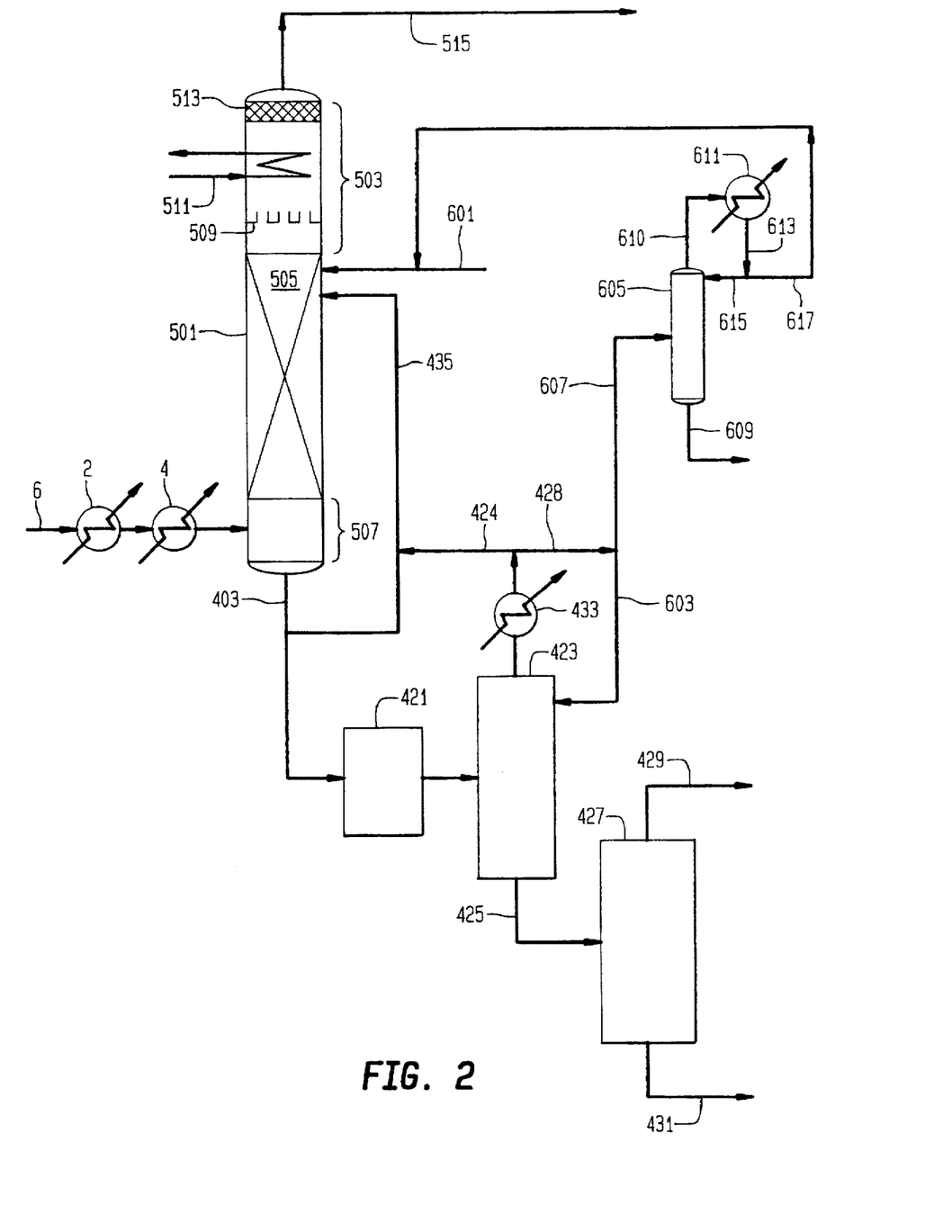
FIG. 2 is a schematic diagram of the phthalic anhydride recovery process in accordance with another embodiment of the present invention wherein an integrated contactor/condenser rectification tower includes an internal reflux section for recycling refluxed low freezing point solvent and by-products to the rectification section.
Figure 3:
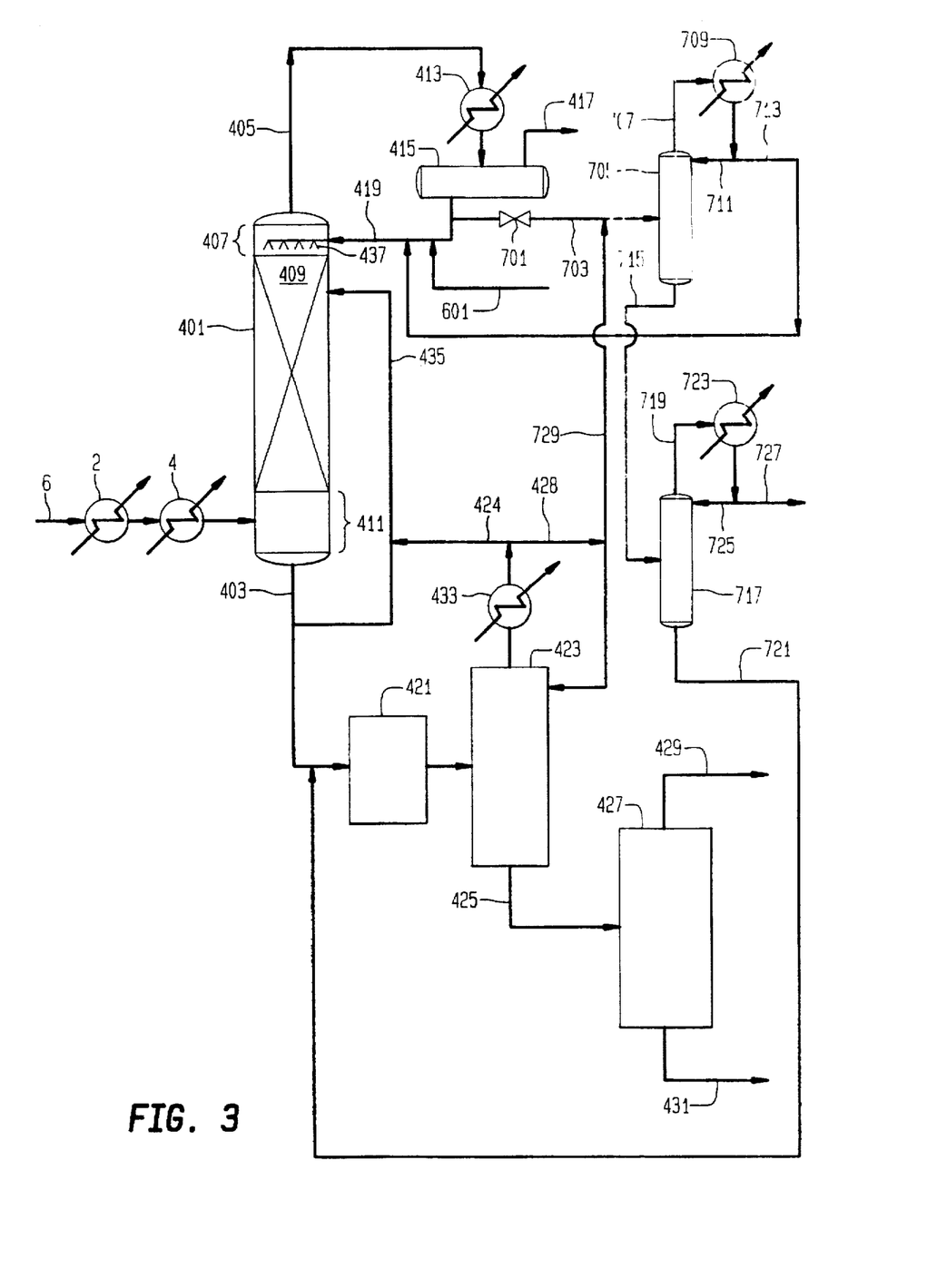
FIG. 3 is a schematic diagram of the phthalic anhydride recovery process disclosed in FIG. 1 above having benzoic acid reflux concentration control.

The low solvent addition case according to the present invention involves the configurations depicted in FIGS. 1 and 2. These figures pertain to the use of a contacting or packed tower having either an internal or external cooling/condensing system. FIG. 3 depicts the unique process that can be used to remove benzoic acid from the vapor phase overheads taken from the processes described in FIGS. 1 and 2.

FIG. 1 describes a process for recovering phthalic anhydride as a liquid from a vapor phase oxidation product. The vapor phase oxidation product of o-xylene, naphthalene, and/or any other material capable of being catalytically converted to phthalic anhydride is passed via conduit 6 through heat exchangers 2 and 4 wherein the vapor phase oxidation product is cooled to a temperature of about 130° C. (266° F.) or greater. Temperatures higher than 130° C. are less desirable because the additional heat is rejected to cooling water and greater rectifier condenser surface area is required. The cooled vapor phase oxidation product is delivered from conduit 6, following cooling to a temperature no lower than about 130° C., to rectifier or contacting means 401 which is capable of causing the vapor phase oxidation product to come into contact with a solvent having a boiling point in the range between about 150° to 350° C. and a freezing point of less than 40° C. and at least one by-product stream having a freezing point which is lower than the freezing point of pure phthalic anhydride and so that a vapor-to-liquid weight ratio in the range between about 2 to 20 is maintained, thereby forming a liquid phase phthalic anhydride product having a phthalic anhydride concentration of between about 50–100 wt. %, preferably between about 85–100 wt. %, more preferably about 90–100 wt. %, and most preferably between about 95–99.8 wt. %, and a first vapor stream. Rectification tower 401 separates the liquid phase phthalic anhydride product from the first vapor stream by means of multiple equilibrium stages, i.e., packing or trays, (not shown) disposed therein. Rectifier tower 401 is typically a low pressure drop counter-current gas/liquid contactor having at least 2 low pressure drop equilibrium stages, preferably 3 to 10.

It should be kept in mind that despite operating below the freezing point of phthalic anhydride there is no formation of a solid phase anywhere within rectifier tower 401 due to the choice of operating conditions.

The liquid phase phthalic anhydride product is removed from rectifier tower 401 as bottoms via conduit 403, while the first vapor stream is removed from rectifier tower 401 as overhead via conduit 405. Rectifier tower 401 has an upper section 407, an intermediate section 409 and a lower section 411.

The first vapor stream taken overhead via conduit 405 is passed through a heat exchanger or low pressure drop gas cooler 413 where it is cooled to a temperature in the range between about 25° C. to 80° C. (77°–176° F.), thereby forming a first by-product stream, a solvent stream and a second vapor stream. This mixed phase stream is then delivered to a vapor/liquid disengaging drum 415 (with or without a de-entrainment screen) wherein the first by-product stream and solvent stream are separated from the second vapor stream. The second vapor stream is then taken out overhead via conduit 417 for either maleic recovery (for sales) or disposal via incineration. At least a portion of the first by-product stream and the solvent stream are taken out as bottoms from drum 415 via conduit 419 and recycled as reflux to upper section 407 of rectifier tower 401. The first by-product stream preferably contains about 40 to 95 mole % maleic anhydride, about 0 to 20 mole % citraconic anhydride, about 0 to 50 mole % phthalic anhydride, and about 0 to 35 mole % benzoic acid.

If it is determined that the first by-product stream and solvent stream from drum 415 do not contain sufficient solvent and lower freezing point by-products, e.g., maleic anhydride and citraconic anhydride, then make-up solvent can be delivered to top section 407 of rectifier tower 401 via conduits 601 and 419. The first by-product stream will freeze if the maleic anhydride to phthalic anhydride ratio in the first by-product stream is less than or equal to 0.07 to 1. The addition of sufficient solvent to lower the freezing point of the first by-product stream will avoid freezing thereof and allow the liquid phthalic anhydride recovery process according to the present invention to occur continuously.

The liquid phase phthalic anhydride product which is removed from rectifier tower 401 as bottoms preferably has a concentration of between about 50–100 wt. %, more preferably between about 90–100 wt. %, and most preferably between about 95–99.8 wt. %, phthalic anhydride.

The liquid phase phthalic anhydride product passes via conduit 403, optionally, into at least one decomposer 421 which operates under a slight vacuum (about 700 mm Hg absolute) and high temperatures (e.g., 260° C. (500° F.) to convert the small amount of phthalic acid that is present to phthalic anhydride. Thereafter, the liquid phase phthalic anhydride product is pumped from decomposer 421 to a light ends column or fractionation column 423 wherein a second by-product stream comprising low-boiling by-products, e.g., maleic anhydride, citraconic anhydride and benzoic acid, along with a small amount of solvent and phthalic anhydride are removed at the top of fractionation column 423, cooled via heat exchanger 433, and at least a part of this stream is optionally returned to rectifier tower 401 as a second by-product stream via conduits 424 and 435 with the remainder of the stream being recycled via conduit 428 to remove benzoic acid and recover solvent. Crude phthalic anhydride is taken as bottoms from fractionation column 423 and is optionally fed via conduit 425 to a second fractionation column 427 wherein substantially pure phthalic anhydride is removed from the top of fractionation column 427 via conduit 429, while heavy products are removed from the bottom via conduit 431.

Optionally, a small portion (i.e., 0–50%) of the liquid phase phthalic anhydride product removed as bottoms from rectifier tower 401 via conduit 403 is recycled via conduit 435 to rectifier tower 401 for temperature and concentration control in the tower.

It is also optional to take the overhead streams from fractionation tower 423 and either reflux these overhead streams back to tower 423 via conduits 428 and 603 or direct the overhead streams to distillation tower 605 via conduits 428 and 607. The overhead streams from tower 423 are then separated in tower 605 to form an overhead stream consisting primarily of a solvent, maleic anhydride, citraconic anhydride and a benzoic acid purge stream. The benzoic acid purge stream is taken as bottoms from tower 605 via conduit 609. The solvent stream taken overhead from tower 605 via conduit 610 is condensed via heat exchanger 611. The condensed solvent is then recycled to tower 605 via conduits 613 and 615 and taken to tower 401 via conduits 613, 617 and 419 in order to reduce the amount of make-up solvent (i.e., solvent delivered via conduit 601) which is required by the system to keep the liquid distillate (i.e., solvent and first by-product stream) in tower 401 from freezing.

FIG. 2 depicts an integrated rectifier tower/cooler condenser unit 501 which may be used in place of rectifier tower 401, cooler 413 and separator 415 of FIG. 1. Integrated rectifier tower/cooler condenser unit 501 comprises a upper section 503, an intermediate section 505 and lower section 507.

Vapor phase oxidation product is carded via conduit 6 through heat exchangers 2 and 4 where it is cooled to a temperature no lower than about 130° C. or greater before being sent to lower section 507 of integrated rectifier unit 501. Intermediate section 505 of integrated rectifier tower/cooler condenser unit 501 comprises a low pressure drop gas/liquid contactor having at least 2, preferably 3 to 10 equilibrium stages. Upflowing cooled vapor phase oxidation product contacts a downflowing recycled by-product stream and a solvent having a boiling point in the range between about 150° to 350° C. and a freezing point of less than 40° C. from upper section 503 as it passes through intermediate section 505 causing liquid phase phthalic anhydride to return to lower section 507 while a first vapor phase stream passes through liquid redistributor 509 into upper section 503. While in upper section 503, the first vapor stream is cooled via cooling coils 511 to a temperature in the range between about 25° C. to 80° C., thereby forming a solvent and first by-product stream, and a second vapor stream. The solvent and first by-product stream are returned or recycled to the liquid redistributor and thereafter flow downwardly into intermediate section 505 so as to come into contact with upflowing vapor phase oxidation product, as discussed above. The second vapor stream passes through a vapor/liquid disengaging section disposed at the top of upper section 503. The disengaging section may optionally include a de-entrainment screen 513 wherein any residual liquid phase first by-product stream is separated from the second vapor stream before the second vapor stream is taken overhead via conduit 515 for either maleic recovery (for sales) and/or incineration.

The liquid phase containing phthalic anhydride passes through integrated rectifier unit 501 in a downward direction until it reaches lower section 507 where it is removed from integrated rectifier unit 501 as bottoms via conduit 403. The liquid phase phthalic anhydride product is then finished in decomposer 421, fractionation tower 423 and fractionation tower 427 as described above.

Overall recovery of the phthalic anhydride from the reactor effluent gas (i.e., vapor phase oxidation product) is approximately 99.7% for both processes described in FIGS. 1 and 2.

It is also optional to take the overhead streams from fractionation tower 423 and either reflux these overhead streams back to tower 423 via conduits 428 and 603 or direct the overhead streams to distillation tower 605 via conduits 428 and 607. The overhead streams from tower 423 are then separated in tower 605 to form an overhead stream consisting primarily of a solvent and a benzoic acid purge or bottoms stream. The benzoic acid purge stream is taken as bottoms from tower 605 via conduit 609. The solvent stream taken overhead from tower 605 via conduit 610 is condensed via heat exchanger 611. The condensed solvent is then recycled to tower 605 via conduits 613 and 615 and taken to tower 501 via conduits 613, 617 and 601 in order to reduce the amount of make-up solvent (i.e., solvent delivered via conduit 601) which is required by the system to keep the liquid condensate in section 503 from freezing.

Optionally, maleic anhydride in the second vapor phase stream may be recovered in accordance with the unique maleic anhydride recovery process depicted in co-pending U.S. Patent Applications, Ser. No. 08/241/876, filed May 12, 1994, and Ser. No. 08/431,647, filed May 2, 1995, both of which are incorporated herein by reference.

FIG. 3 discloses substantially the same liquid phthalic anhydride recovery process as described above in FIG. 1, wherein a solvent having a boiling point in the range between about 150° to 350° C. and a freezing point of less than 40° C. is added to the eutectic mixture in tower 401 to prevent its freezing up. The difference between FIGS. 1 and 3 is the addition of a benzoic acid recovery step, wherein the solvent and first by-product stream taken from dram 415 via conduit 419 is diverted via valve 701 and conduit 703 to a distillation tower 705. Tower 705 takes the solvent, maleic anhydride and/or citraconic anhydride overhead via conduit 707, cools the overhead stream via heat exchanger 709 and either recycles the refluxed overheads to tower 705 via conduit 711 and sends tower 705 distillate to tower 401 via conduits 713 and 419. The bottoms from tower 705 which comprise substantially benzoic acid and phthalic anhydride are taken via conduit 715 and passed to distillation tower 717 wherein benzoic acid is taken overhead via conduit 719 and phthalic anhydride is taken as bottoms via conduit 721. The benzoic acid taken overhead is condensed via heat exchanger 723 and recycled to tower 717 via conduit 725 and purged from the system via conduit 727. The phthalic anhydride stream taken as bottoms via conduit 721 is admixed with the bottoms taken from tower 401 via conduit 403 and passed to decomposer 421.

FIG. 3 optionally provides for the recapture of additional solvent by taking at least a portion of the condensed overhead stream from conduit 428 and passing it to tower 705 via conduit 729, wherein benzoic acid is removed from the system and solvent is recycled to tower 401 via conduit 713. It should be understood that the embodiments set forth in FIG. 3 are also applicable to FIG. 2 in the instance where it is desirable to have a rectification tower design such as that depicted in FIG. 2 combined with a benzoic acid removal system as shown in FIG. 3.

Figure 4:
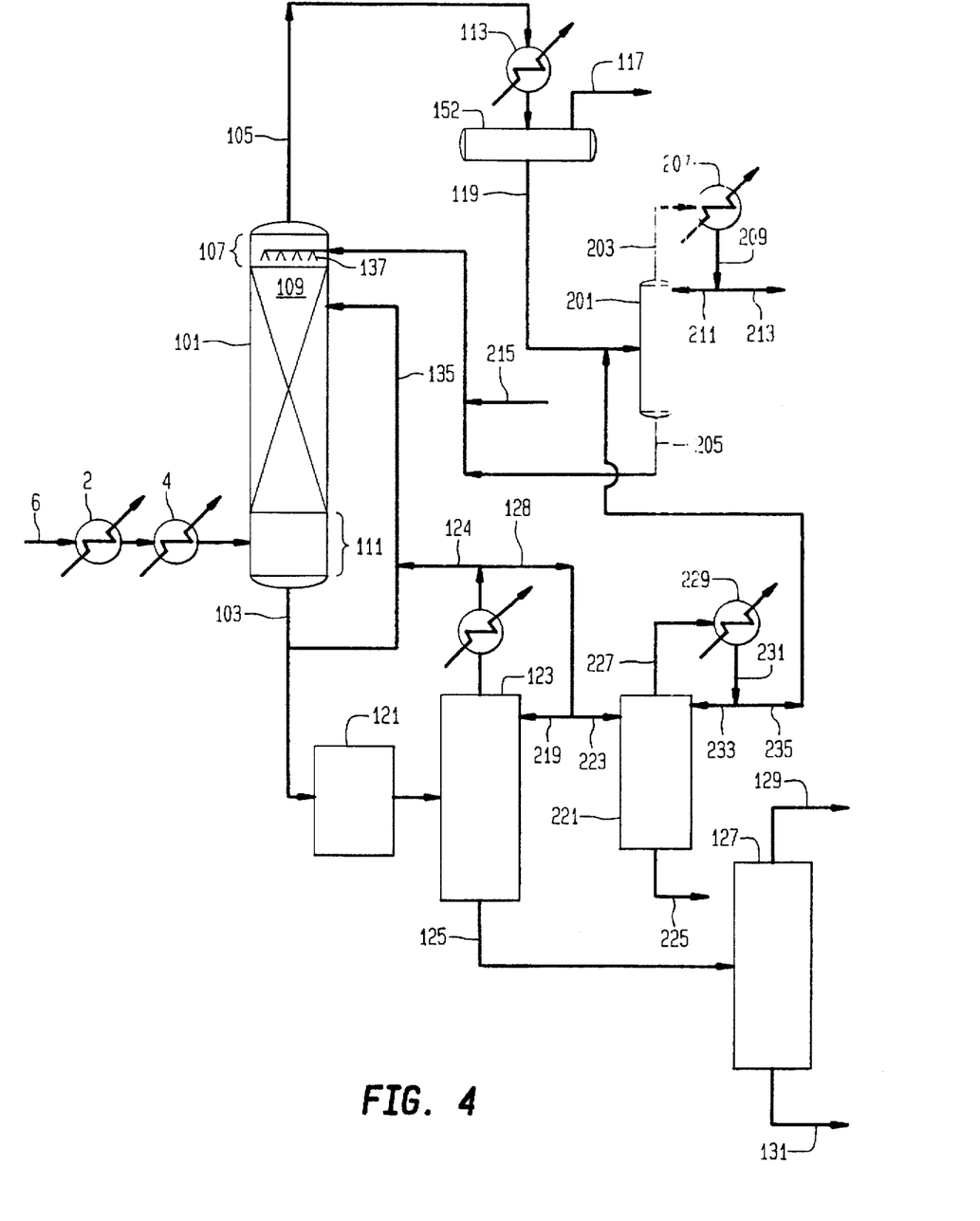
FIG. 4 is a schematic diagram of the phthalic anhydride recovery process in accordance with the preferred embodiment of the present invention wherein a low pressure gas/liquid contactor rectification tower is used in conjunction with external cooling and separating devices for recycling a low freezing point solvent back to the rectification tower without by-product recycle.
Figure 5:
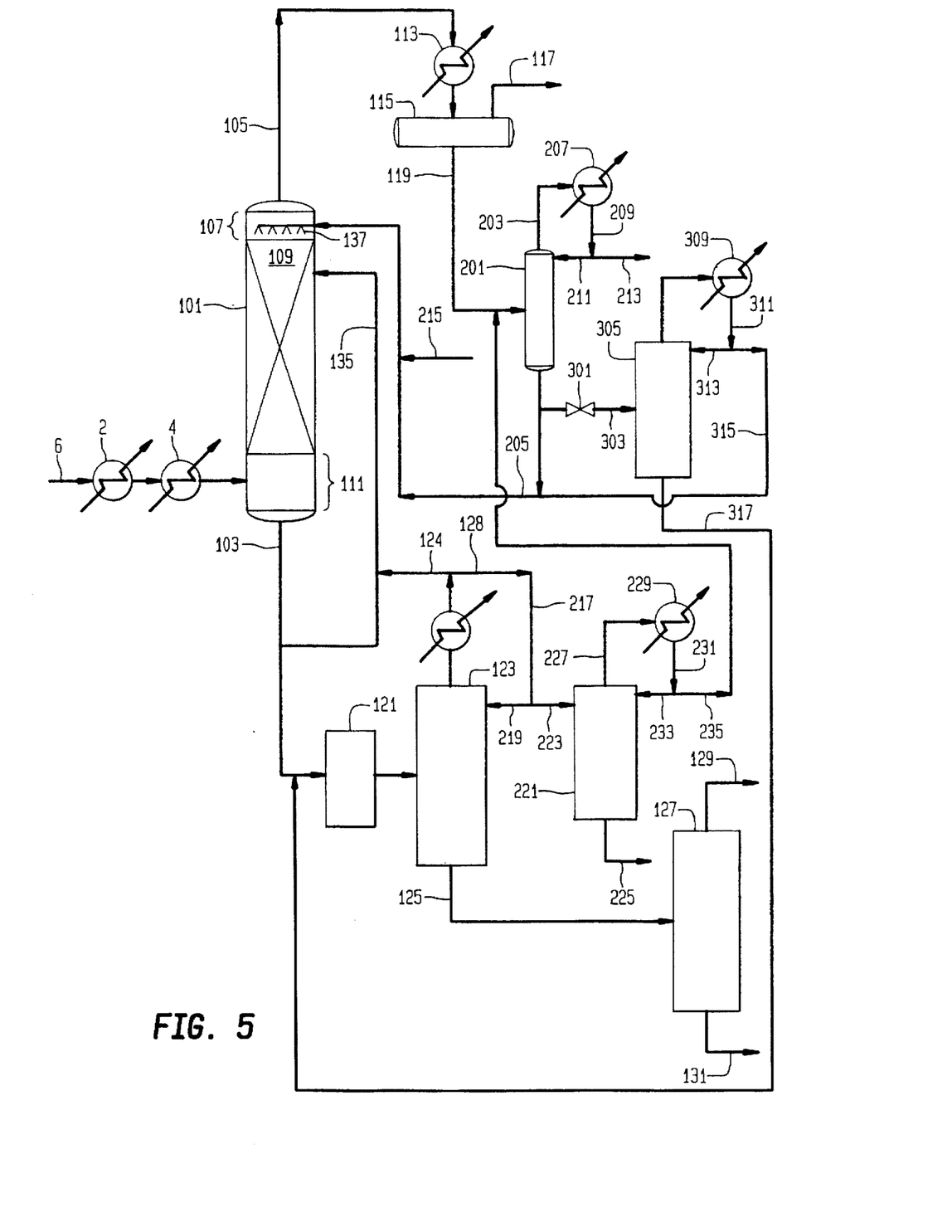
FIG. 5 is a schematic diagram of the phthalic anhydride recovery process disclosed in FIG. 4 above having benzoic acid reflux concentration control.

The high solvent or substantially all solvent addition case is depicted in FIGS. 4 and 5. FIG. 4 describes a process for recovering phthalic anhydride as a liquid from a vapor phase oxidation product. The vapor phase oxidation product of o-xylene, naphthalene, and/or any other material capable of being catalytically converted to phthalic anhydride is passed via conduit 6 through heat exchangers 2 and 4 wherein the vapor phase oxidation product is cooled to a temperature of about 130° C. (266° F.) or greater. Temperatures higher than 130° C. are less desirable because the additional heat is rejected to cooling water and greater rectifier condenser surface area is required. The cooled vapor phase oxidation product is delivered from conduit 6, following cooling to a temperature no lower than about 130° C., to rectifier or contacting means 101 which is capable of causing the vapor phase oxidation product to come into contact with a solvent having a boiling point in the range between about 150° to 350° C. and a freezing point of less than 40° C. so that a vapor-to-liquid weight ratio in the range between about 2 to 20 is maintained, thereby forming a liquid phase phthalic anhydride product having a phthalic anhydride concentration of between about 50–100 wt. %, preferably between about 85–100 wt. %, more preferably about 90–100 wt. %, and most preferably between about 95–99.8 wt. %, and a first vapor stream. Rectification tower 101 separates the liquid phase phthalic anhydride product from the first vapor stream by means of multiple equilibrium stages, i.e., packing or trays, (not shown) disposed therein. Rectifier tower 101 is typically a low pressure drop counter-current gas/liquid contactor having at least 2 low pressure drop equilibrium stages, preferably 3 to 10.

It should be kept in mind that despite operating below the freezing point of phthalic anhydride there is no formation of a solid phase anywhere within rectifier tower 101 due to the choice of operating conditions.

The liquid phase phthalic anhydride product is removed from rectifier tower 101 as bottoms via conduit 103, while the first vapor stream is removed from rectifier tower 101 as overhead via conduit 105. Rectifier tower 101 has an upper section 107, an intermediate section 109 and a lower section 111.

The first vapor stream taken overhead via conduit 105 is passed through a heat exchanger or low pressure drop gas cooler 113 where it is cooled to a temperature in the range between about 25° C. to 80° C. (77°–176° F.), thereby forming a first by-product stream, a solvent stream and a second vapor stream. This mixed phase stream is then delivered to a vapor/liquid disengaging drum 115 wherein the first by-product stream and solvent stream are separated from the second vapor stream. The second vapor stream is then taken out overhead via conduit 117 for either maleic recovery (for sales) or disposal via incineration. The first by-product stream and the solvent stream are taken out as bottoms from drum 115 via conduit 119 and delivered to a fractionation or distillation tower 201, wherein maleic anhydride and/or citraconic anhydride are taken overhead via conduit 213 and the solvent, benzoic acid and/or residual phthalic anhydride are taken as bottoms via conduit 205.

The first by-product stream preferably contains about 40 to 95 mole % maleic anhydride, about 0 to 20 mole % citraconic anhydride, about 0 to 50 mole % phthalic anhydride, and about 0 to 35 mole % benzoic acid.

The overhead stream taken from fractionation tower 201 via conduit 203 is preferably cooled via heat exchanger 207 and either recycled to the top of tower 201 via conduits 209 and 211 or purged from the system via conduits 209 and 213. The bottoms from fractionation tower 201 are preferably recycled to top portion 107 of rectification tower 101 in order to maintain the proper vapor to liquid ratio therein such that the freezing point of the PAN/MAN/benzoic acid (BA) mixture is lowered, thereby avoiding freezing and providing a larger operating range in rectification tower 101. If necessary, make-up solvent can be added to rectification tower 101 via conduits 215 and 205.

The liquid phase phthalic anhydride product which is removed from rectification tower 101 as bottoms preferably has a concentration of between about 50–100 wt. %, more preferably between about 90–100 wt. %, and most preferably between about 95–99.8 wt. %, phthalic anhydride.

The liquid phase phthalic anhydride product passes via conduit 103, optionally, into at least one decomposer 121 which operates under a slight vacuum (about 700 mm Hg absolute) and high temperatures (e.g., 230° C. (200° F.)) to convert the small mount of phthalic acid that is present to phthalic anhydride. Thereafter, the liquid phase phthalic anhydride product is pumped from decomposer 121 to a light-ends column or fractionation column 123 wherein a second by-product stream comprising low-boiling by-products, e.g., maleic anhydride, citraconic anhydride and/or benzoic acid, along with a small amount of phthalic anhydride are removed at the top of fractionation column 123, cooled via heat exchanger 133, and at least a part of this stream is optionally returned to rectifier tower 101 as a second by-product stream via conduits 124 and 135 with the remainder of the stream being either recycled to the top of fractionation column 123 via conduits 128 and 219 and sent to a second fractionation column 221 via conduits 128 and 223. The second by-product stream sent to fractionation column 221 is separated into a benzoic acid purge stream and a solvent-enriched stream. The benzoic acid purge stream is taken as bottoms via conduit 225 and the solvent-enriched stream is taken overhead via conduit 227, cooled via heat exchanger 229 and recycled to the top of tower 221 via conduits 231 and 233 and sent to fractionation tower 201 via conduits 231, 235 and 119, wherein the solvent-enriched stream can be recycled to rectification tower 101.

Crude phthalic anhydride is taken as bottoms from fractionation column 123 and is optionally fed via conduit 125 to fractionation column 127 wherein substantially pure phthalic anhydride is removed from the top of fractionation column 127 via conduit 129, while heavy products are removed from the bottom via conduit 131.

Optionally, a small portion (i.e., 0–10%) of the liquid phase phthalic anhydride product removed as bottoms from rectifier tower 101 via conduit 103 is recycled via conduit 135 to rectifier tower 101 for temperature and concentration control in the tower.

FIG. 5 discloses substantially the same liquid phthalic anhydride recovery process as described above in FIG. 4, wherein a solvent having a boiling point in the range between about 150° to 250° C. and a freezing point of less than 40° C. is added to the eutectic mixture in rectification tower 101 to prevent its freezing up. The difference between FIGS. 4 and 5 is the addition of a benzoic acid recovery step, wherein the solvent, phthalic anhydride and benzoic acid stream taken as bottoms from fractionation tower 201 via conduit 205 are diverted via valve 301 and conduit 303 to another fractionation tower 305. Fractionation tower 305 separates by means of distillation the bottoms stream taken from tower 201 into a solvent-enriched stream and a benzoic acid-enriched stream. The solvent-enriched stream is taken overhead via conduit 307, cooled via heat exchanger 309 and either recycled to tower 305 via conduits 311 and 313 or returned to top portion 107 of rectification tower 101 via conduits 311, 315 and 205. The benzoic acid-enriched stream which comprises primarily benzoic acid and phthalic anhydride is blended with the liquid phthalic anhydride stream taken as bottoms from rectification tower 101 via conduits 317 and 103, and thereafter sent to decomposer 121.

FIG. 5 optionally provides for the recapture of additional solvent by taking at least a portion of the condensed overhead stream from conduit 128 and passing it to tower 221 via conduits 217 and 223, wherein benzoic acid is removed from the system and solvent is recycled to tower 201 as described above in FIG. 4.

EXAMPLE 1

Table 1 below demonstrates how a specifically tailored solvent according the present invention is capable of markedly lowering liquid mixture freezing points even at high benzoic acid concentrations.

TABLE 1

| Sample (°C.) | PAN | BA | MAN | CAN | DMA* | Freezing Point |
|---|---|---|---|---|---|---|
| 1 | 1.0 | 1.4 | 4.9 | 0.7 | 0 | 65 |
| 2 | 1.0 | 1.4 | 4.9 | 0.7 | 0.4 | 62 |
| 3 | 1.0 | 1.4 | 4.9 | 0.7 | 2.0 | 39 |
| 4 | 1.0 | 1.4 | 4.9 | 0.7 | 5.4 | 13 |

*denotes a solvent of di-methyl adipate.

All component amounts are based on mole/mole of PAN.

The following examples demonstrate the principal of using a solvent in the liquid phthalic anhydride recovery process to depress the freezing point.

EXAMPLE 2

Table 2 below demonstrates how a specifically tailored solvent according the present invention is capable of markedly lowering liquid mixture freezing points at low benzoic acid concentrations.

TABLE 2

| Sample | PAN | BA | MAN | CAN | Solvent | Freezing Pt. (°C.) |
|---|---|---|---|---|---|---|
| 1 | 1.0 | 0.45 | 6.1 | 0.75 | 0 | 34 |
| 2 | 1.0 | 0.45 | 6.1 | 0.75 | 1.7* | 25 |
| 3 | 1.0 | 0.45 | 6.1 | 0.75 | 1.7** | 27 |

*denotes a solvent of di-methyl adipate.
**denotes a solvent of aromatic 200.

All component amounts are based on mole/mole of PAN.

EXAMPLE 3

Table 3 below demonstrates how a specifically tailored solvent according the present invention is capable of markedly lowering liquid mixture freezing points.

TABLE 3

| Sample | PAN | BA | MAN | CAN | Solvent | Freezing Pt. (°C.) |
|---|---|---|---|---|---|---|
| 1 | 1.0 | 0.5 | 6.1 | 0.8 | 0 | 34 |
| 2 | 1.0 | 0.5 | 6.1 | 1.3 | 0 | 32 |
| 3 | 1.0 | 0.5 | 6.1 | 0.8 | 0.54* | 32 |
| 4 | 1.0 | 0.5 | 6.6 | 1.0 | 1.7* | 28 |
| 5 | 1.0 | 0.5 | 6.1 | 0.8 | 0.54** | 32 |
| 6 | 1.0 | 0.5 | 6.1 | 0.8 | 0.54*** | 32 |
| 7 | 1.0 | 0.5 | 6.1 | 0.8 | 0.54**** | 31.7 |
| 8 | 1.0 | 0.5 | 6.1 | 0.8 | 0.54***** | 32 |
| 9 | 1.0 | 0.5 | 6.6 | 1.0 | 1.7****** | 34 |

*denotes a solvent of propylene carbonate.
**denotes a solvent of di-ethyl adipate.
***denotes a solvent of n-butyl benzoate.
****denotes a solvent of $C_{10}$ acetate ester.
*****denotes a solvent of isophorone.
******denotes a solvent of isophorone undecane.

All component amounts are based on mole/mole of PAN.

Reducing benzoic acid, as in Table 3 above, lowers freezing points verses Table 1 above.

EXAMPLE 4

Table 4 below demonstrates how a specifically tailored solvent according the present invention can be used to replace MAN/BA/CAN to markedly lower the mixture freezing point.

TABLE 4

| Sample | PAN | BA | MAN | CAN | Solvent* | Freezing Pt. (°C.) |
|---|---|---|---|---|---|---|
| 1 | 1.0 | 0.5 | 6.1 | 0.8 | 0 | 34 |
| 2 | 1.0 | 0.0 | 0.0 | 0.0 | 5.0 | <<28 |

*denotes a solvent of propylene carbonate.

As clearly demonstrated above, when the reflux from the condenser system disposed overhead of the rectification tower comprises solvent rather than MAN, BA and CAN the freezing point is lowered from 34° C. for the base case to less than 82° C. for the high solvent assisted case (Example 4, Sample 2).

EXAMPLES 5 AND 6

To demonstrate the invention, a gas phase o-xylene oxidation reactor effluent (containing the components produced by a commercial PAN catalyst system) shown as stream 6 on FIG. 1 was fed to the bottom of a pilot plant rectification tower. Reflux shown as stream 419 was fed to the top of the tower. The temperature of the feed gas stream was 162° C. The rectification tower in this experiment was a 25.4 mm (1 inch) vacuum jacketed column containing a 914 mm (36 inch) section of stainless steel structured packing. Based on manufacturer estimates, the packing provided about 7–14 equilibrium stages.

The reflux stream composition for the non-solvent case (Example 5) was determined by modeling the rectification process based on the organic by-products in PAN reactor effluent gas and on the literature and theoretical vapor-liquid equilibrium data. For the solvent assisted case (Example 6) the reflux composition was set to be the limiting case of pure solvent. In actual practice, this solvent reflux stream would contain other oxidation products such as maleic anhydride, phthalic anhydride and benzoic acid.

As shown by Examples 5 and 6, a crude liquid phthalic anhydride bottoms stream was produced having a composition of about 99% PAN. Crude liquid phase phthalic anhydride from the pilot plant rectification tower and crude phthalic anhydride produced commercially using switch condensers were both heat treated in the laboratory under standard commercial heat treatment ("Decomposer") conditions. Following heat treatment, the samples were distilled in a laboratory apparatus designed to simulate commercial distillation. Sales quality PAN was obtained from all samples.

These pilot plant results demonstrate that phthalic anhydride can be recovered with or without the assistance of a solvent in high concentrations from a rectification tower and that this recovered product can be finished into sales grade phthalic anhydride.

In addition, Examples 5 and 6 clearly demonstrate the principal of the liquid phthalic anhydride recovery process, i.e., recovery of phthalic anhydride via distillation in the rectification section of a distillation tower. In both Examples 5 and 6 the PAN in the vapor phase oxidation product is transferred to the liquid phase and the lower boiling reflux components (either solvent or a mixture of MAN, CAN and BA) are transferred from the liquid phase to the vapor phase. The solvent assisted process has a particular advantage since the addition of the solvent lowers the freezing point of the condensate obtained when the rectification tower overhead stream is cooled. This freezing point depression widens the operating window in the condenser by increasing the temperature difference between the condensate temperature and its' freezing point.

TABLE 5

| Example 5 | | | | | | |
|---|---|---|---|---|---|---|
| Reflux to tower | 246 g/hr | | | | | |
| Gas feed to tower | 1852 g/hr | | | | | |
| Gas/liquid ratio weight ratio in tower | 7.5 grams gas/grams liquid | | | | | |
| Organics Composition | PAN | MAN | CAN | BA | PHD** | DMA* |
| (moles) | | | | | | |
| Reflux | 1.00 | 5.8 | 0.84 | 0.43 | 0.00 | none |
| Gas feed | 1.00 | 0.055 | 0.005 | 0.009 | 0.001 | none |
| Bottoms Product | 1.00 | 0.005 | 0.002 | 0.003 | 0.001 | none |
| Example 6 | | | | | | |
| Reflux to tower | 246 g/hr | | | | | |
| Gas feed to tower | 1670 g/hr | | | | | |
| Gas/liquid ratio weight ratio in tower | 6.8 grams gas/grams liquid | | | | | |

TABLE 5-continued

| Organics Composition | PAN | MAN | CAN | BA | PHD** | DMA* |
|---|---|---|---|---|---|---|
| (moles) | | | | | | |
| Reflux | 0 | 0 | 0 | 0 | 0 | 1.000 |
| Gas feed | 1.00 | 0.055 | 0.005 | 0.009 | 0.001 | 0.000 |
| Bottoms Product | 1.00 | — | — | 0.002 | 0.001 | 0.0014 |

*denotes dimethyl adipate
**denotes phthalide

EXAMPLE 7

The data set forth in Table 6 below clearly demonstrates the effect which the maleic anhydride to phthalic anhydride ratio in the vapor phase oxidation product feed into the contacting tower has on the freezing point in the liquid condensate generated from the overhead vapor phase taken from the contacting tower.

TABLE 6

| LOADING (grams)* | MAN/PAN RATIO | FREEZING POINT (°C.) |
|---|---|---|
| 72 | 0.059 | 35.00 |
| 80 | 0.057 | 36.67 |
| 100 | 0.045 | 37.22 |

*Phthalic anhydride reactor loading based upon grams of o-xylene per NM$^3$ wet air.

The preferred freezing point of the liquid condensate from the overhead vapor phase is typically between about 41.67 to 43.89° C. (107° to 111° F.). Therefore, the higher the molar ratio of MAN/PAN, the lower the freezing point of the liquid condensate from the overhead vapor phase and the further away from the freezing point of phthalic anhydride.

When the freezing point of the liquid condensate approaches or exceeds the target freezing point of between about 41.67° to 43.89° C. (107° to 111° F.), then it is required to add a solvent to the liquid phthalic anhydride recovery system according to the present invention to avoid the freezing of the condensate and the shutting down of the system. The solvent of the present invention is added to the eutectic mixture in the contact tower to lower the freezing point of the liquid condensate generated from the overhead vapor phase.

This unique process may also be extended to recover other anhydrides and acids such as maleic anhydride, trimellitic anhydride, pyromellitic anhydride, benzoic acid etc. from vapor phase oxidation products without the formation of a solid phase intermediate.

What is claimed is:

1. A process for recovering phthalic anhydride as a liquid from a vapor phase oxidation product having a lower maleic anhydride to phthalic anhydride ratio which comprises mixing said vapor phase oxidation product having a temperature of about 130° C. or greater with a first stream comprising a solvent having a boiling point in the range between about 150° to 350° C. and a freezing point of less than 40° C. in a contacting means such that a substantial portion of the phthalic anhydride contained within said vapor phase oxidation product transfers from the vapor phase to a liquid phase and a substantial portion of said first stream which is more volatile than phthalic anhydride transfer from the liquid phase to the vapor phase by-product and wherein a vapor-to-liquid weight ratio in the range between about 2 to 20 is exhibited within said contacting means, thereby forming a liquid phase phthalic anhydride product having a phthalic anhydride concentration in the range between about 50-100 wt. %.

2. The process according to claim 1 wherein said first stream further comprises at least one by-product selected from the group consisting of: maleic anhydride, citraconic anhydride, benzoic acid, ortho-tolualdehyde and phthalic anhydride.

3. The process according to claim 1 wherein said solvent is at least one solvent selected from the group consisting of: adipates, carbonates, benzoates, ketones, aromatics, anhydrides, esters, halogenated hydrocarbons, halogenated oxy hydrocarbons, ether acetates, naphthalenes, and ethers.

4. The process according to claim 3 wherein said solvent is at least one solvent selected from the group consisting of: dimethyl adipate, propylene carbonate, propyl benzoate, isobutyl benzoate, isophorone, e-caprolaetone, isobutyl heptyl ketone, di-normal amyl ketone, di-isoamnyl ketone, hexyl benzene, mixed aromatics, n-valeric anhydride, $C_9$ alky acetate ester, $C_{10}$ alky acetate ester, 1,4-butanediol diacetate, malonic acid-dipropyl ester, dimethyl phthalate, dimethyl maleate, diethyl maleate, and an ester formed from the reaction product of $C_5$ to $C_{10}$ neo acids and $C_2$ to $C_{10}$ monohydride or polyhydric alcohols.

5. The process according to claim 1 further comprising the steps of:
 removing said vapor phase by-product from said contact means;
 cooling said vapor phase by-product to form a vapor stream and a liquid condensate; and
 separating said vapor stream from said liquid condensate.

6. The process according to claim 5 wherein said maleic anhydride to phthalic anhydride ratio in said vapor phase oxidation product is sufficient to cause freezing in said condenser liquid.

7. The process according to claim 6 wherein said maleic anhydride to phthalic anhydride ratio in said vapor phase oxidation product is less than or equal to 0.07 to 1.

8. A process for recovering phthalic anhydride as a liquid from a vapor phase oxidation product which comprises:
 (a) cooling said vapor phase oxidation product to a temperature of about 130° C. or greater; and
 (b) delivering said vapor phase oxidation product to a contacting means which is capable of causing said vapor phase oxidation product to come into contact with a solvent having a boiling point in the range between about 150° to 350° C. and a freezing point of less than 40° C. and at least one by-product stream having a freezing point which is lower than the freezing point of pure phthalic anhydride such that a substantial portion of the phthalic anhydride contained within said vapor phase oxidation product transfers from the vapor phase to a liquid phase and a substantial portion of said solvent and by-product stream is more volatile than phthalic anhydride transferred from the liquid phase to the vapor phase and wherein a vapor-to-liquid weight ratio in the range between about 2 to 20 is exhibited within said contacting means, thereby forming a liquid phase phthalic anhydride product having a phthalic anhydride concentration in the range between about 50 to 100 wt. %, and a first vapor stream.

9. The process according to claim 8 wherein said contacting means is also capable of separating said liquid phase phthalic anhydride product from said first vapor stream.

10. The process according to claim 8 wherein said solvent has a boiling point in the range between about 200° to 285° C.

11. The process according to claim 10 wherein said solvent has a boiling point in the range between about 213° to 270° C.

12. The process according to claim 8 wherein said solvent is at least one solvent selected from the group consisting of: adipates, carbonates, benzoates, ketones, aromatics, anhydrides, esters, halogenated hydrocarbons, halogenated oxy hydrocarbons, ether acetates, naphthalenes, and ethers.

13. The process according to claim 8 wherein said contacting means is either a rectification tower, wetted wall reactor or counter-current reactor.

14. The process according to claim 12 wherein said solvent is at least one solvent selected from the group consisting of: dimethyl adipate, propylene carbonate, propyl benzoate, isobutyl benzoate, isophorone, e-caprolactone, isobutyl heptyl ketone, di-normal amyl ketone, di-isoamyl ketone, hexyl benzene, mixed aromatics, n-valeric anhydride, $C_9$ alky acetate ester, $C_{10}$ alky acetate ester, 1,4-butanediol diacetate, malonic acid-dipropyl ester, dimethyl phthalate, dimethyl maleate, diethyl maleate, and an ester formed from the reaction product of $C_5$ to $C_0$ neo acids and $C_2$ to $C_{10}$ monohydric or polyhydric alcohols.

15. The process according to claim 8 further comprising the steps of:
(c) removing said liquid phase phthalic anhydride product from said contacting means as bottoms;
(d) removing said first vapor stream from said contacting means as overhead;
(e) cooling said first vapor stream to a temperature in the range between about 25° C. to 80° C., thereby forming said solvent, a first by-product stream and a second vapor stream;
(f) separating said solvent and said first by-product stream from said second vapor stream; and
(g) recycling at least a portion of said solvent and said first by-product stream to the upper section of said contacting means.

16. The process according to claim 15 wherein said first by-product stream comprises about 40 to 95 mole % maleic anhydride, about 0 to 20 mole % citraconic anhydride, about 0 to 50 mole % phthalic anhydride, and about 0 to 35 mole % benzoic acid.

17. The process according to claim 15 wherein said solvent is present in an amount between about 1 to 50 mole %, based upon the total amount of said solvent and said first by-product stream recycled under step (g).

18. The process according to claim 15 further comprising the addition of make-up solvent.

19. The process according to claim 15 wherein said maleic anhydride to phthalic anhydride ratio in said vapor phase oxidation product is sufficient to cause freezing in said first by-product stream.

20. The process according to claim 19 wherein said maleic anhydride to phthalic anhydride ratio in said first by-product stream is less than or equal to 0.07 to 1.

21. The process according to claim 15 further comprising the steps of:
(h) diverting at least a portion of said first by-product stream and said solvent;
(i) separating the diverted first by-product stream and solvent into a third vapor phase comprising at least solvent and maleic anhydride and a second by-products stream comprising at least benzoic acid; and
(j) recycling said third vapor phase to the upper section of said contacting means.

22. The process according to claim 21 further comprising the steps of:
(k) separating said second by-products stream into a benzoic acid vapor phase and a phthalic anhydride residue stream; and
(m) combining said phthalic anhydride residue stream with said liquid phase phthalic anhydride product.

23. The process according to claim 15 further comprising the step of recycling between about 0 to 50 wt. % of said liquid phase phthalic anhydride product of step (c) to said contacting means, whereby said liquid phase phthalic anhydride product is only used for temperature and composition control.

24. The process according to claim 8 further comprising the following steps:
(c) cooling said first vapor stream to a temperature in the range between about 25° C. to 80° C. in the upper section of said contacting means, thereby forming said solvent, a first by-product stream and a second vapor stream;
(d) separating said solvent and said first by-product stream from said second vapor stream in said upper section; and
(e) transferring said solvent and said first by-product stream to the top of said contacting means;
(f) removing said liquid phase phthalic anhydride product from said contacting means as bottoms; and
(g) removing said second vapor stream from said contacting means as overhead.

* * * * *